July 1, 1947. J. E. WILTGEN Plant Pat. 740
ROSE PLANT
Filed May 23, 1946
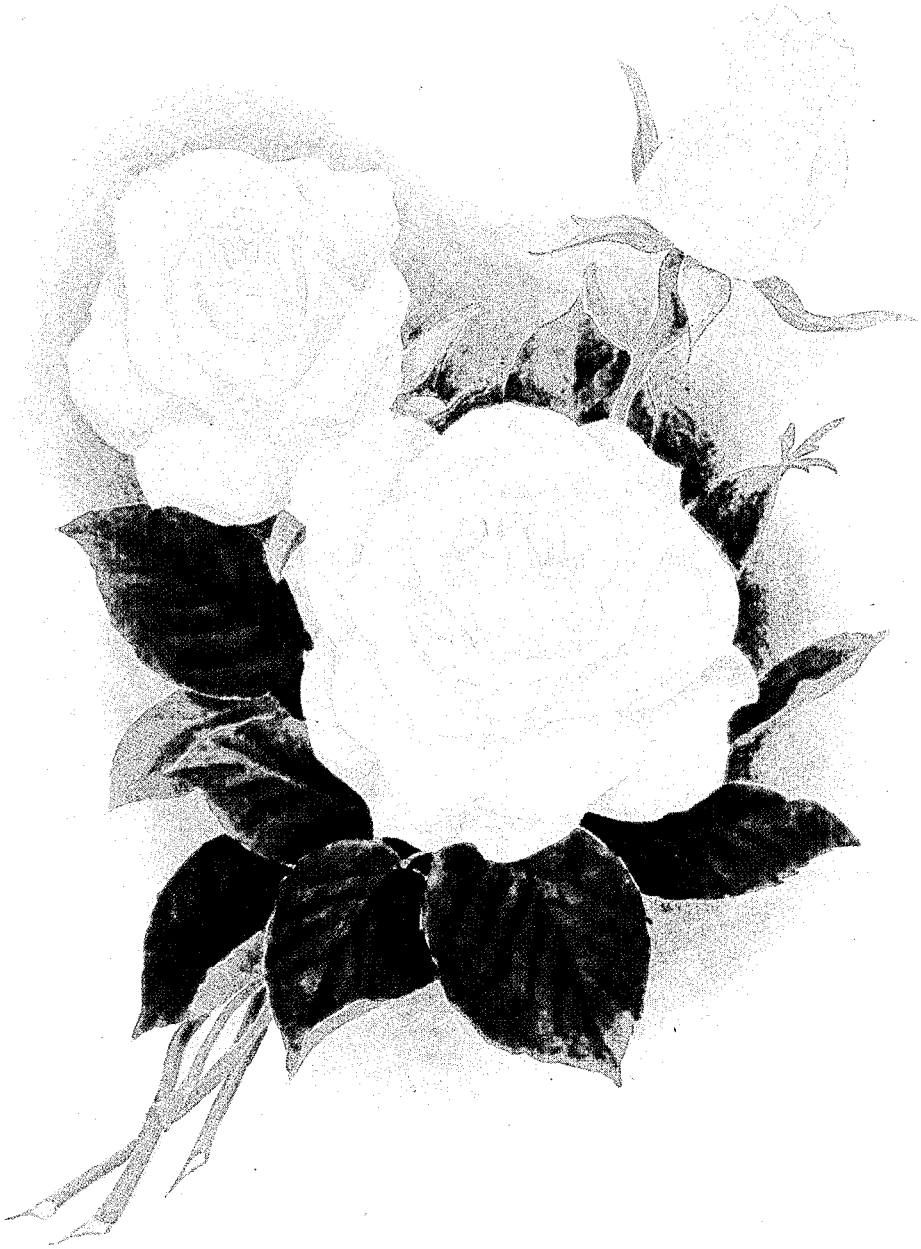
WITNESS
Addison J. Avery
INVENTOR
JOSEPH E. WILTGEN,
by Rummler, Rummler & Davis,
ATTYS.

Patented July 1, 1947

Plant Pat. 740

UNITED STATES PATENT OFFICE

740

ROSE PLANT

Joseph E. Wiltgen, Park Ridge, Ill., assignor to The Premier Rose Gardens, Consolidated, Des Plaines, Ill., a corporation of Illinois Application May 23, 1946, Serial No. 671,757

1 Claim. (Cl. 47—61)

The new variety of rose plant herein described and illustrated is a sport, discovered by me at Premier Rose Gardens, Des Plaines, Illinois, of the well-known rose "Pink Delight," which parent variety was imported from Kordes, Germany, and originated as a cross between "Senator" and "Florex." My new variety has been asexually reproduced by budding and grafting since October, 1944, and its characteristics appear to be permanently fixed. At the present time there are 10,000 plants of this variety in the greenhouses at Des Plaines, Illinois.

The primary object in carrying out this invention was to establish the exquisitely warm pink, uniform color of this rose which is largely the distinguishing characteristic of the new variety. The new plant grows vigorously, blooms freely and continuously and the cut flower has long-lasting qualities. The petals do not fall off until the life of the bloom is spent. It is a thriving, healthy plant, free from the usual diseases common to roses.

The accompanying illustration shows in full color specimens of this new variety in various stages of development.

Referring to the novel characteristics of this new variety, the flower is a large semi-double to double blossom of uniform pink coloring, shading from the deep pink of the compact central grouping of petals to the delicate, light pink of the outer petals. The petals have a suede-like inner surface texture, thus giving the bloom a soft pink sheen, and although the inner or upper surface of the petals has a substantially uniform intensity of coloring throughout the visible portions thereof, the darker pink under surface of the petals acts to reflect a deeper color glowing through the pockets formed by the whorls of petals. The marginal portions of the petals curl outward in two or more lobal areas on each petal and produce high lights and shades of great beauty. The under surface of the petals is covered by a fine network of branching veins radiating from the stem. In the fullblown rose, the petals disposed themselves so as to leave the high center compact and outstanding. In the very last stages of the bloom, the stigmas and anthers show as a delicate touch of yellow coloring, while the flower retains its characteristic pink shading.

There is a sufficient quantity of large, dark green foliage to give a pleasing green background to the blooms. The calyx forms a five-pointed star-like base cup for both the bud and the opening rose.

My new variety is a freer bloomer than its parent "Pink Delight" and its coloring is a more delicate shade of pink. Every bud opens up after cutting, and the blooms will outlast most roses. The plant maintains the same pink coloring of blooms throughout the year despite cloudy weather. The corolla is borne on sturdy upright stems; and there are no weak-necked ones.

The following is a detailed description of my new variety:

*Flower*

Blooming habit is recurrent and freer growing than parent.

Bud:

*Form.*—Urn-shape.

*Color.*—All-over rich pink shade.

Bloom:

*Size.*—Partly opened, 1½ inches in diameter by 1¼ inches in depth; fully blown, 3½ inches in diameter by 1½ inches in depth.

*Borne.*—Singly.

*Petal texture.*—Suede-like surface.

*Stems.*—Sturdy and long without pinching; 3 or more feet in length.

*Discoloration.*—None.

*Affected by wet or hot weather.*—No; maintains same color throughout the year despite cloudy weather.

*Fragrance.*—Delicate rose.

*Lasting quality.*—Will outlast most roses; every bud opens up after cutting.

*Plant*

Foliage:

*Quantity.*—Sufficient.

*Color.*—Yellow-green.

*Size of full grown leaf.*—2¾ inches x 1¾ inches.

*Texture.*—Smooth, firm.

*Thorns.*—1 or 2 toward base of stem.

The color designations according to "A Dictionary of Color by Maerz and Paul" are as follows:

| Part | Plate | Letter | No. |
|---|---|---|---|
| Main body color of flower | 41 | I | 1 |
| Shading out to | 41 | D | 1 |
| Bud and outer face of petal | 41 | J | 1 |
| Main leaf green | 24 | L | 5 |
| Under side of leaf | 21 | D | 6 |
| Calyx | 21 | L | 6 |
| Stem | 21 | L | 6 |

The suede-like texture of the petals, their distinctive soft pink coloring, compact centers, their sturdy stems, together with their superior keeping qualities, abundance of blooms, resistance to disease and weather, combine to enhance the value of this plant as a commercial product.

Having thus disclosed the invention, I claim:

A new and distinct variety of rose plant, substantially as shown and described, characterized particularly by its vigorous growth; its continuous and exceptionally free blooming habits; sturdy stems; and the soft pink color of its blooms with the inner surface of its petals a pale pink and the outer surface a deeper shade of pink.

JOSEPH E. WILTGEN.